United States Patent [19]

Brockbank

[11] Patent Number: 5,071,741
[45] Date of Patent: Dec. 10, 1991

[54] CRYOPROTECTIVE AGENT AND ITS USE IN CRYOPRESERVATION OF CELLULAR MATTER

[75] Inventor: Kelvin G. M. Brockbank, Marietta, Ga.

[73] Assignee: Cryolife, Inc., Marietta, Ga.

[21] Appl. No.: 182,367

[22] Filed: Apr. 18, 1988

[51] Int. Cl.$^5$ ............................................. A01N 1/00
[52] U.S. Cl. ......................................... 435/1; 435/2; 436/18; 128/898; 128/DIG. 27; 62/62
[58] Field of Search ................... 435/2, 260, 1; 62/62; 436/8, 10, 18; 128/898, DIG. 27

[56] References Cited

U.S. PATENT DOCUMENTS

| | | | |
|---|---|---|---|
| 3,303,662 | 2/1967 | Moline et al. | 62/62 |
| 3,758,382 | 9/1973 | Knorpp | 435/2 |
| 4,004,975 | 1/1977 | Lionetti et al. | 435/29 |
| 4,097,338 | 6/1978 | Konttinen et al. | 436/18 |
| 4,237,218 | 12/1980 | Mothony et al. | 435/2 |
| 4,473,552 | 9/1984 | Jost | 435/2 |
| 4,489,162 | 12/1984 | Hawkins et al. | 436/10 |
| 4,559,298 | 12/1985 | Fahy | 435/1 |
| 4,840,891 | 6/1989 | Van Blerkom | 435/2 |
| 4,874,690 | 10/1989 | Goodrich et al. | 435/2 |

*Primary Examiner*—David L. Lacey
*Assistant Examiner*—William Chan
*Attorney, Agent, or Firm*—Kenyon & Kenyon

[57] ABSTRACT

A novel class of nonpermeating cryoprotectants which, when mixed with certain known penetrating cryoprotectants, provide a useful medium for protection of living cells during a cryopreservation process. Algae-derived polysaccharides such as agarose and alginate are useful as nonpermeating cryoprotectants as they form a gel matrix when cooled, protect against ice crystal formation, and yield improved viability of cells when thawed.

28 Claims, No Drawings

CRYOPROTECTIVE AGENT AND ITS USE IN CRYOPRESERVATION OF CELLULAR MATTER

TECHNICAL FIELD

The present invention relates to the field of cryopreservation. More specifically, disclosed is a novel class of nonpermeating cryoprotectants which can be used in combination with a permeating cryoprotectant to provide protection of living cells during the cryopreservation process, yielding improved viability.

BACKGROUND OF THE INVENTION

At the outset several terms should be defined. "Cellular matter" or "cell" refers to a living structure, composed of a mass of protoplasm, enclosed in a membrane and containing a nucleus. It may or may not be part of a larger structure. "Tissue" means a collection of similar cells and the intercellular substances surrounding them. There are four basic tissues in the human body: (1) epithelium; (2) connective tissues, including blood, bone and cartilage; (3) muscle tissue; and (4) nerve tissue. "Cryoprotectant" refers to chemical compounds which are added to biological samples in order to minimize the deleterious effects of cryopreservation procedures. "Osmotic effects" refers to the alteration in the osmotic strength of the suspending media caused by conversion of water to ice or ice to water. This conversion results in substantial flow of water across membranes of unfrozen cells, causing volume changes during freezing and thawing. "Viability" refers to the ability of frozen and thawed cells to perform their normal functions. Viability is usually expressed as the ability of the cells to reproduce, metabolize, exclude vital dyes or carry out some other metabolic function. The viability of the frozen and thawed samples should always be compared to the ability of unfrozen cells obtained at the same time to carry out the same function.

There has been an increase in recent years of person willing to donate various organs for transplantation or research purposes. Along with this national networks have been created to match available organs with needy recipients, resulting in a growing need to store organs for extended periods of time. In 1987 there will have been approximately 400,000 transplantation and implantation procedures, involving such tissues as heart valve, cornea, pancreas, skin, blood vessel, tendon/ligament, bone, bone marrow, nerve and others. The major advances in transplantation of tissues are occurring because of efficient sterile procurement techniques, recognition of a group of immunologically privileged tissues, development of techniques for the avoidance of the transplant recipient's immune surveillance system, and improvements in tissue preservation methods. Storage of this tissue has become more important to enable physicians to procure and match tissues with recipients.

Historically, several approaches for tissue storage have been used. The most commonly used and promising method has been cryopreservation. Some alternative method has been cryopreservation. Some alternative methods have been freeze drying, chemical treatment, tissue culture prior to transplantation, and storage at refrigeration temperatures. Storage at refrigeration temperatures is acceptable for short periods of time, but can result in reduced viability of the tissue if stored too long. Freezing protocols must be designed to optimize tissue viability. These methods, if not properly controlled, can lead to cell damage.

Two major mechanism for injury to cells and tissues during freezing have been emphasized. First, there are the obvious mechanical injuries which can occur due to either extra or intracellular ice crystal formation. Second, there is the danger of osmotic dehydration. Current cryopreservation technology consists of trying to maintain a balance between these two forms of injury. Basically, when freezing is performed at a rapid rate, there is a tendency for ice crystals to form both intracellularly and extracellularly. However, when cryopreservation is performed at slower rates, there is a tendency for ice crystal formation to occur first in the extracellular medium. As the extracellular ice forms, the cells are exposed to an increasingly hyperosmotic environment. This is due to water sequestration as the ice crystals grow. The cells shrink due to transport of water out of the cell in response to the osmotic imbalance caused by the increasing extracellular solute concentrations. The net result of combining optimal cooling rates and cryoprotective agents is that less of the freezable intracellular water will be converted to ice and osmotic cellular dehydration is limited.

The field of cryopreservation dates from 1949, when Polge, Smith, and Parkes discovered the protective properties of glycerol for bull sperm [*Nature* 164;666 (1949)] Subsequently, in 1959, Lovelock and Bishop [*Nature* 183:1394 (1959)] reported the protective activities of dimethysulfoxide ("DMSO") is preventing freezing injury to living cells. DMSO and glycerol have since become the most widely utilized cryoprotectant.

Permeating cryoprotective agents, such as DMSO and glycerol, act by penetrating the cell membrane and reducing the intracellular water concentration, thereby reducing the amount of ice formed at any temperature.

There are a variety of so-called nonpermeating protective agents. These agents include such compounds as polyvinylpyrrolidone, hydroxyethyl starch, monosaccharides, and sugar alcohols. In addition, both permeating and nonpermeating cryoprotectants act directly on the cell membranes. The mechanism of the nonpermeating cryoprotectants is not clear, but may involve changes in colloidal osmotic pressure and modifications of the behavior of membrane associated with water by ionic interaction. For some cells, combination of these two classes of cryoprotective agents may give optimal viability.

There is a need, then, for an agent that can overcome the problems of ice crystal formation, toxicity and osmotic dehydration possible during the cryopreservation process. Such an agent would be nontoxic to the tissue or cell, inexpensive to obtain, and convenient to use.

SUMMARY OF THE INVENTION

The present invention relates to a novel class of compounds useful in the cryoprotection of living cells and tissues. More particularly, the present invention comprises the use of algae-derived polysaccharides as a class of nonpermeating cryoprotectants. These naturally occurring polysaccharides, known as agaroses and alginates, can be isolated from certain algae. These substances are biomedically important, because, while remaining biologically inert, they can form a gel matrix for diffusion and electrokinetic movement of water and biopolymers. It is believed that the gel matrix organizes the extracellular water and therefore enforces a less destructive order on the ice formed during cooling and warming. These polysaccharides are readily available in dry powder form and are easily prepared as a solution.

Non-permeating cryoprotectants in general apparently act on the cell membrane. This protection may be due to colloidal osmotic pressure forces exerted by large molecules and alterations in the activity of the unfrozen intercellular water caused by hydrogen bonding of these molecules to water.

In accordance with the present invention algae-derived polysaccharides are used in conjunction with a permeating cryoprotectant such as DMSO or glycerol. Permeating cryoprotectants are effective in minimizing damage to slowly frozen biological systems. By replacing water as an intracellular fluid with DMSO deleterious ice crystal formation is reduced. The combination of an algae-derived polysaccharide and a permeating cryoprotectant act to provide a novel cryoprotectant with a synergistic protective effect.

It is therefore a principal object of the present invention to provide a cryoprotectant agent providing improved protection of frozen cellular matter.

It is another object of the present invention to provide a cryoprotectant agent comprising at least one algae-derived polysaccharide in combination with a permeating cryoprotectant.

It is another object of the present invention to provide a cryoprotectant agent comprising agarose or alginate in combination with DMSO or glycerol.

It is another object of the present invention to provide a cryoprotectant agent for use in a process of cryopreserving viable cells or tissue.

It is yet another object of the present invention to provide a cryoprotectant agent for use in cryopreserving islets of Langerhans.

It is a further object of the present invention to provide a cryoprotectant agent which will reduce intracellular and extracellular ice crystal formation during the cryopreservation process.

It is yet another object of the present invention to provide a cryoprotectant agent which will reduce the extent of cellular osmotic dehydration during the cryopreservation process.

It is still another object of the present invention to provide an improved method for cryopreserving living cells.

It is another object of the present invention to provide a method of preparing cells for cryopreservation with improved post-thaw viability of the cells or tissue.

It is yet another object of the present invention to provide a method for transplanting living cells from a donor to a recipient body with improved viability of the received cells or tissue.

DESCRIPTION OF THE INVENTION

The present invention relates broadly to the field of cryopreservation, and more particularly to the use of macromolecular polysaccharides as a nonpermeating cryoprotectant when used in conjunction with a permeating cryoprotectant.

The macromolecular polysaccharide is composed of nonhydrolyzed saccharide molecules linked together to form long chains. The macromolecule can be composed of from about three to 3,000 saccharide molecules, more preferably from about 300 to 1200. In a preferred embodiment algae-derived polysaccharides are used. These include agarose and alginate.

Agarose is derived from agar, which is extracted from various types of red algae seaweed belonging to the group Rhodophyceae. Structurally, agarose is a purified linear galactan hydrocolloid. Different agarose preparations vary significantly with respect to their physical and chemical properties, depending upon the genus of Rhodophyta used.

Alginates are derived from algin, obtained from the brown seaweeds of the group Phaeophyceae. Alginate is extracted from seaweed with a strong solution of a sodium salt. Alternatively, alginic acid may be reduced with bases to give the salts and reacted with propylene oxide to make propylene glycol alginate. Both Rhodophceae and Phaeophceae seaweeds grow off the coasts of most continents. The giant kelp *Macrocystis pyrifera*, which grows in abundance along the coasts of North and South America, New Zealand, Australia and Africa, is one of the principal sources of the world's supply of algin.

Algin is composed of three kinds of polymer segments. One segment consists essentially of D-mannuronic acid units connected by B-1-4 linkages; a second segment consists essentially of L-glucuronic acid units; and the third segment consists of alternating D-mannuronic acid and L-glucuronic acid residues.

One of the most useful properties of agaroses and alginates is their ability to form gels by reaction with divalent cations or by cooling. A gel is defined as a system which resembles a solid in its ability to retain its shape, and resist stress owing to a cross-linked network of polymer chains which form at gelpoints. The gel consists of about 97.5% to 99% water plus solutes and 0.3 to 2.5% polymer.

When gelled, these polysaccharides are useful as nonpermeating cryoprotectants because they provide protection for the cell. It is believed that the gel matrix orders extracellular ice formation in a manner which results in less mechanical ice-induced tissue damage. The gel matrix allows for diffusion and electrokinetic movement of water and biopolymers, while remaining essentially biologically inert.

The permeating cryoprotectant of the present invention is any suitable material, preferably glycerol or DMSO or combinations thereof. The concentration of glycerol can range from about 0.5 to 3 molar, preferably about 1 molar. DMSO is highly permeable to the cell membranes and usually can be mixed directly with the samples at the appropriate concentrations or added stepwise. Stepwise addition may reduce the possibility of osmotic shock to the cell due to sharp increases in the extracellular osmolarity. It is preferable, but not mandatory, to perform the cryoprotectant addition steps at a low temperature (4° C. or lower), because the agents are often toxic to the cell if added at room temperature. The length of time required for osmotic equilibrium at 4° C. is substantially longer than at 37° C., but this may result in less stress to the cell and therefore higher viability.

In accordance with the present invention a solution comprising a mixture of algae-derived polysaccharide and DMSO is prepared. The solution in which the tissue is frozen is of great important for maintaining a balanced cell environment. Time and temperature also contribute to whether a particular medium will be successful. Generally, a protein suspension, such as blood serum or artificial serum, must also be present for maximum cell viability.

A number of freezing media can be successfully used in practicing the present invention. Media such as balanced tissue culture medium or simple phosphate buffered saline can be used for most tissue types. Dulbecco's Minimum Essential Medium ("DMEM") is the preferred medium plus fetal calf serum ("FCS") of from about 1% to 30%, more preferably 10% FCS and algae derived polysaccharide having a concentration of from about 0.05% to 5%, preferably 0.1% to 3%, more preferably 0.2% to 2%.

DMSO is also added either in at least one step of 1M or preferably in three steps of 0.25M, 0.5M, and 1M titrations at 4° C. Concentrations of DMSO can range from about 0.5 to 3 molar. The increase in molarity of DMSO should preferably be gradual so as not to traumatize the tissue. DMSO can be added at higher temperatures but timing becomes far more critical and toxicity may result in some tissues.

Examples of other suitable co-cryoprotectants include, but are not limited to, hyaluronic acid, dermatan sulfate, heparin sulfate, chondroitin sulphate, and heparin, glycerol, polyvinyl pyrrolidone, hydroxyethyl starch, polyethylene glycol, dimethylformamide, ethyl glycol and the like.

A variety of cellular and tissue matter can be cryoprotected using the composition of the present invention. Such living matter includes, but is not limited to, islets of langerhans, endothelial cells, saphenous veins, arteries, heart valves, liver cells, heart valves, corneas, pancreas, skin, bond marrow, nerve, connective tissue such as ligaments, tendons and cartilage, endocrine and exocrine glands, and the like.

The present invention also comprises a method for cryopreserving viable cellular matter using the cryoprotectant disclosed herein. The cryopreservation process includes the general steps of (1) preparing the cellular matter with a cryoprotectant; (2) freezing the cells; (3) storing the frozen cells; and (4) thawing the cells. In transplantation, the cells or tissue are recovered from a donor body or other source and cryopreserved. Following thawing of the material and removal of the cryoprotectants, the cells or tissues are implanted in a recipient body. In order to obtain maximum cell viability, the cryopreservation process must be carefully controlled and monitored. Each type of cell or tissue has a unique freezing and thawing profile based on the particular intracellular makeup, intercellular organization, and the types and concentrations of cryoprotectants employed. An example of a particular freezing profile for blood vessels is disclosed in commonly assigned copending application Ser. No. 088,092, filed Aug. 21, 1989 (which is expressly incorporated by reference herein).

The rate of change from room temperature to 1-2° C. below the freezing point of the solution may have a major effect on ultimate viability if the cells are sensitive to thermal shock. Between 3.5° C. and −5° C., the sample is normally induced to freeze either by the introduction of an ice crystal, by touching the surface of the media with a cold probe, by mechanical vibration, or by rapidly lowering the temperature until ice nucleation occurs. Since freezing is an exothermic process, heat must be conducted away from the freezing solution. This may be done either by keeping the samples immersed in a liquid with a low freezing point or by providing a substantial heat sink. As ice forms in the extracellular media, more and more free water becomes bound in the ice phase. Cell membranes, being hydrophobic, act as a barrier for the nucleation of intracellular ice and therefore unfrozen cells are exposed to an increasingly hypertonic solution. The extracellular salt concentration increases as a consequence of water sequestration into ice. The unfrozen cells shrink due to the transport of water out of the cell in response to the osmotic imbalance between the intracellular and extracellular fluid phases. The sample is then cooled at a finite rate which must be optimized for each cell type.

The optimal rate of cooling is determined by the permeability of the cell membrane to water, the surface-to-volume ratio of the cell, along the type and concentration of cryoprotective additives. For most nucleated mammalian cells frozen in glycerol or DMSO, the optimal cooling rate usually is between about 0.3° to 10° C. per minute. Continuous cooling between about 4° C. and −80° C. is the most commonly used. Once the sample reaches approximately −80° C., it can be transferred directly into liquid nitrogen (−196° C.) or into the vapor phase of liquid nitrogen for storage.

The duration of viable cell storage at liquid nitrogen temperature is dependent predominantly on the rate of generation of free radicals caused by the cosmic ray background. For example, the half-life for mammalian embryos stored in liquid nitrogen has been estimated to be approximately 30,000 years. It is important not to allow frozen cells to warm above their storage temperature for even brief periods of time. Intermittent warming promotes rapid migratory recrystallization, which can damage cellular structure and decrease overall viability.

The optimal rate of thawing of the sample is dependent on the freezing conditions used. In general, for single cells frozen in suspension, and for tissues such as heart valves, a rapid rate of warming is desirable. Such rapid warming limits the growth of ice crystals in the frozen samples and is often an absolute requirement for high survival. With many tissues this warming can be accomplished by agitating the sample in a 37°–42° C. water bath. The rationale for rapid warming is that it limits the growth of ice crystals which were formed during cooling. Some tissues may be sensitive to rapid warming. This is due to transient osmotic shock, because the cells are exposed to an extracellular hypertonic solution as the ice melts and are forced to rehydrate in order to maintain their osmotic equilibrium. For other, more sensitive, samples, metabolic processes can be reactivated or brought up to normal levels by successive dilutions using serum or other high molecular weight polymers in the thawing medium.

Upon completion of the thawing procedure, the cells are still exposed to multimolar concentrations of cryoprotective agents which must be gradually diluted to return the cells to an isotonic media. This also reduces dilution induced osmotic shock. For mammalian cells, a stepwise dilution protocol is typically used. The dilution of the sample is normally carried out at preferably 4° C., so as to reduce the effects of both osmotic shock and cryoprotectant toxicity. When glycerol is used, care must be taken to insure complete mixing of the physiological salt solution with the cryoprotective solution. Overly rapid dilution can result in the cells being exposed to a potentially damaging osmotic stress while very slow dilution may result in toxicity to the cells from prolonged exposure to the cryoprotective agent(s).

One of the most crucial factors in any cryobiological procedure is defining the term "viability". That definition should include one or more critical functions that accurately reflect how the cell normally carries out its biological function. The ultimate test for viability is the reproduction of the cell through two or more generations after freezing. Thus, in the case of mammalian embryos, the birth of a healthy animal (or person) is a far more definitive assay than quantitative changes in, for example, cytochrome B reductase levels. For many cell types, however, assays of cell division are not practical. For example, since polymorphonuclear leukocytes do not divide, other integrated structure/function assays must be used. For these cells, assays for chemotaxis, phagocytosis, reduction of nitroblue tetrazolium dye or the generation of superoxide radicals are more appropriate because they require that both the structural cellular machinery and the cellular enzymatic systems be intact. For relatively simple, organized tissues such as islets of Langerhans, the release of insulin in response to a differential glucose challenge is an excellent indication of functional viability.

In an alternative embodiment the present invention can be used in a method for transplanting cryopreserved cellular matter from a donor body to a recipient body. In accordance with such a method cellular matter is first removed from a donor using standard removal techniques. Then an effective amount of algae-derived polysaccharide is added to the cell mass which is then gelled by cooling or by adding divalent cations. A penetrating cryoprotectant is added to the gel-enclosed cellular matter and then frozen according to an appropriate freezing profile. The frozen cells are stored in appropriate container until they are to be transplanted.

The frozen cells are thawed when needed for transplantation. The thawed cells are encapsulated according to known procedures in order to reduce the likelihood of rejection or creating an immune response by the recipient. The encapsulated cells are implanted in the recipient by standard techniques. This transplantation method is particularly useful with islets of Langerhans.

The invention will be further described in connection with the following examples which are set forth for purposes of illustration only.

EXAMPLES

EXAMPLE 1

A solution of 0.45 agarose was made in culture medium containing 10% fetal calf serum and 1 molar DMSO. This solution was added to cultures of adherent bovine endothelial cells from a bovine aortic endothelium-derived cell line, known as BFA-clone 1. The cultures were then cryopreserved at a cooling rate in the range of 3° to 5° C. per minute to −60° C., held for at least one hour, and then thawed in a 37° C. waterbath. The results of nine experiments are summarized in Table 1.

TABLE 1

| Effect of Agarose (0.45%) on Cell Survival | |
|---|---|
| | Viability |
| control (without cryoprotectants) | 2% |
| + agarose | 3% |
| + 1M DMSO | 39% |
| + 1M DMSO and agarose | 69% |

Data pooled from nine experiments.
Viability determined by the acridine orange/propidium iodide technique.

The experimental cultures, cryopreserved with agarose and 1 molar DMSO, had a mean of 69% of their cells viable after thawing, while cultures containing b 1 molar DMSO without agarose contained a mean of only 39% viable cells. Cultures containing agarose without 1 molar DMSO and cultures containing neither agarose nor 1 molar DMSO had less than 5% viable cells. These experiments demonstrate clearly the cryoprotectant nature of agarose in conjunction with 1 molar DMSO.

EXAMPLE 2

Droplets, 500 to 700 microns in diameter, of alginate containing aggregates of islets of Langerhans derived from murine pancreas were encapsulated with poly-L-lysine by the process previously described in Lim (U.S. Pat. No. 4,409,331 which is incorporated by reference herein). The encapsulated islet cells were then placed in a solution containing 10% fetal calf serum and ¼ molar DMSO for 5 minutes. After 5 minutes, the suspension was changed for one containing ½ molar DMSO, and after a further 5 minutes, the encapsulated islets were placed in a final solution of 1 molar DMSO and 10% serum in culture medium. DMSO is freely diffusable in encapsulated islets, and this combination of 1 molar DMSO and alginate permitted successful cryopreservation of the murine islets. The islets were cryopreserved at a rate of approximately 1 degree per minute to −80° C. The islets were then placed into a liquid nitrogen storage tank at −196° C. After two weeks at this temperature, the encapsulated islets were thawed in a 37° C. waterbath, and then the DMSO was removed by gradual dilution with culture medium and 10% fetal calf serum. The capsules were then placed in the peritoneal cavities of C57black/J mice which had previously been made diabetic with the drug Streptozotocin (Sigma Chemical Company, St. Louis, Mo.). An example of the effect of transplantation of cryopreserved islets of Langerhans on blood glucose levels is given in Table 2.

TABLE 2

| Insulin Production by Alginate/DMSO Protected Cryopreserved Islets of Langerhans | |
|---|---|
| | Glucose (mg/dl) |
| Pre-transplant | >400 |
| 1 day post-transplant | 286 |
| 2 days post-transplant | 236 |
| 3 days post-transplant | 171 |
| 4 days post-transplant | 208 |
| 7 days post-transplant | 177 |
| 46 day post-transplant | 217 |

In this mouse, glucose levels were definitely diabetic; i.e., >400 mg/dl of blood prior to transplantation. Thereafter, blood glucose levels were measured at irregular intervals, and on all occasions, the blood glucose levels were in the non-diabetic range, indicating that the cryopreserved islets were functioning, and therefore viable.

It should be noted that consistent maintenance of glucose levels below 300 mg/dl is considered evidence for insulin production by the transplanted islets.

While the invention has been described in conjunction with certain preferred embodiments, it is not intended to limit the scope of the invention to the particular form set forth, but, on the contrary, is intended to cover such alternatives, modifications, and equivalents as may be included as defined by the appended claims.

What is claimed is:

1. A cryoprotective agent comprised of a mixture of a cell-permeating cryoprotectant and a non-cell permeating, macromolecular polysaccharide cryoprotectant derived from algae.

2. The cryopreservative agent of claim 1, wherein said nonpermeating cryoprotectant comprises a mixture of macromolecular polysaccharides.

3. The cryoprotective agent of claim 1 wherein said macromolecular polysaccharide is selected from the group consisting of agarose and alginate.

4. The cryoprotective agent of claim 1 wherein said cell-permeating cryoprotectant is selected from the group consisting of glycerol and dimethylsulfoxide.

5. The cryopreservative agent of claim 4, wherein said cell-permeating cryoprotectant is dimethylsulfoxide and said dimethylsulfoxide is present in a concentration from about 0.5M to 3.0M.

6. The cryopreservative agent of claim 5, wherein said dimethylsulfoxide is present in a concentration of about 1M.

7. A method for cryopreserving viable cellular matter comprising:
(a) treating viable cellular matter with a cryoprotective agent comprising a mixture of a non-cell permeating cryoprotectant and a cell permeating cryoprotectant, said non-cell permeating cryoprotectant comprising an algae-derived macromolecular polysaccharide including from about 3 to about 3000 saccharide units such that said mixture gels at temperatures below ambient or when contacted by divalent ions, said non-cell permeating and cell permeating cryoprotectants being present in the mixture in concentrations effective for enhancing cellular viability upon transplant, and said non-cell permeating cryoprotectant being effective for encapsulating said cellular matter;
(b) freezing said encapsulated cellular matter and
(c) storing said frozen cellular matter.

8. The method of claim 7, wherein said nonpermeating cryoprotectant comprises a mixture of macromolecular polysaccharides.

9. A method of cryopreserving viable cellular matter comprising:
treating viable cellular matter with a cryoprotective agent comprised of a cell-permeating cryoprotectant and a non-cell permeating, algae-derived macromolecular polysaccharide cryoprotectant, and
freezing the treated viable cellular matter to a temperature at least as low as the temperature of nitrogen vapor.

10. The method of claim 9, wherein said macromolecular polysaccharide is composed of a material selected from the group consisting of agarose and alginate.

11. The method of claim 9, wherein said cell-permeating cryoprotectant agent is selected from the group consisting of glycerol and dimethylsulfoxide.

12. The method of claim 11, wherein said dimethylsulfoxide is present in a concentration from about 0.5M to 3M.

13. The method of claim 12, wherein said dimethylsulfoxide is present in a concentration of about 1M.

14. The method of claim 9, wherein said cryopreservative agent comprises at least one algae-derived polysaccharide and dimethylsulfoxide.

15. The method of claim 9, wherein said cellular matter is selected from the group consisting of heart valves, corneas, pancreas, blood vessels, bone, bone marrow, endothelial cells, saphenous veins, liver cells, nerves, connective tissue endocrine glands and exocrine glands.

16. The method of claim 9 wherein said cellular matter is selected from the group consisting of ligaments, tendons and cartilage.

17. The method of claim 9 wherein said cellular matter is skin.

18. The method of claim 9 wherein said cellular matter is islets of Langerhans.

19. In a process for cryopreserving transplantable cellular matter wherein transplantable cellular matter is harvested from a donor and then cryopreserved at a temperature at least as low as the temperature of nitrogen vapor, the improvement comprising the step of encapsulating the transplantable cellular matter in an algae-derived polysaccharide gel prior to cryopreservation.

20. In a process for cryopreserving transplantable cellular matter wherein transplantable cellular matter is harvested from a donor and then cryopreserved at a temperature at least as low as the temperature of nitrogen vapor, the improvement comprising the steps of:
(a) treating the cellular matter with a mixture of at least one algae-derived polysaccharide and dimethylsulfoxide in amounts which are effective for reducing ice crystal formation; and
(b) cooling said treated cellular matter such that a cell is formed around said treated cellular matter.

21. A cryopreservative agent comprising a mixture of a non-cell permeating cryoprotectant and a cell-permeating cryoprotectant,
said non-cell permeating cryoprotectant comprising an algae-derived macromolecular polysaccharide having about 3 to about 3000 saccharide units,
said non-cell permeating and cell permeating cryoprotectants being present in the mixture at concentrations which are effective (a) for forming a gel at a temperature below ambient temperature or upon contact with divalent ions, and (b) improving the biological function of the transplantable, cryopreserved tissue upon transplant into a patient in need of such treatment.

22. A cryoprotective agent of claim 21 wherein the cell-permeating cryoprotectant is dimethylsulfoxide.

23. A method of improving the post-transplantable biological function of a transplantable tissue comprising:
treating the transplantable tissue prior to cryopreservation with a mixture of a non-cell permeating cryoprotectant and a cell-permeating cryoprotectant,
said non-cell permeating cryoprotectant comprising an algae-derived macromolecular polysaccharide containing about 3 to about 3000 saccharide units per molecule,
said non-cell permeating and cell-permeating cryoprotectants being present in the mixture in concentrations which are effective (a) for forming a gel at a temperature below ambient temperature or upon contact with divalent ions, and (b) for improving the biological function of the transplantable, cryopreserved tissue upon transplant into a patient in need of such treatment.

24. A method in accordance with claim 23 further comprising:
encapsulating the transplantable tissue in an algae derived polysaccharide, and
cryopreserving the encapsulated transplantable tissue at a temperature effective for improving the biological function of the tissue.

25. The method of cryopreserving viable cellular matter comprising:

treating viable cellular matter with a mixture of at least one algae-derived macromolecular polysaccharide and dimethylsulfoxide in amounts which are effective for improving the biological function of said cellular matter upon transplant, said algae-derived polysaccharide encapsulating said cellular matter, and freezing said encapsulated cellular matter in said mixture.

26. A method of transplanting cellular matter from a donor into a recipient, comprising:

(a) removing cellular matter from a donor;
(b) treating the cellular matter with a mixture of at least one algae-derived polysaccharide and dimethylsulfoxide in amounts which are effective for improving the biological function of the cellular matter upon subsequent thawing and implant, and for encapsulating said cellular matter with the algae-derived polysaccharide;
(c) freezing said encapsulated cellular matter;
(d) storing said frozen cellular matter;
(e) thawing said frozen cellular matter; and
(f) implanting the thawed cellular matter into the recipient.

27. A method for cryopreserving cellular matter comprising:

(a) removing the cellular matter from a donor;
(b) forming an algae-derived polysaccharide gel around said cellular matter;
(c) adding at least one cell-penetrating cryoprotectant to said gel-enclosed cellular matter in an amount effective for reducing ice crystal formation during cryopreservation, and
(d) storing the cellular matter for a desired period of time.

28. A method of transplanting cellular matter from a donor to a recipient, comprising:

(a) removing cellular matter from a donor;
(b) forming a algae-derived polysaccharide gel around said cellular matter;
(c) adding a cell-penetrating cryoprotectant to the gel-enclosed cellular matter in an amount effective for reducing ice crystal formation;
(d) freezing the gel-enclosed cellular matter and cell-penetrating cryoprotectant;
(e) storing the frozen cellular matter for a desired period of time;
(f) thawing said frozen cellular matter, and implanting the cellular matter in a recipient.

* * * * *

UNITED STATES PATENT AND TRADEMARK OFFICE
CERTIFICATE OF CORRECTION

PATENT NO. : 5,071,741

DATED : December 10, 1991

INVENTOR(S) : Brockbank, Kelvin G.M.

It is certified that error appears in the above-identified patent and that said Letters Patent is hereby corrected as shown below:

In column 1, line 40, please change "person" to -- persons --.

In column 1, line 42, please change "this" to -- this, --.

In column 1, lines 61-62, please delete "Some ... cryopreservation."

In column 2, line 30, please change "is" to -- in --.

In column 2, line 45, please change "membrane" to -- membranes --.

In column 5, line 24, please change "langerhans" to -- Langerhans --.

In column 5, line 25, please delete "heart valves,", second occurrence.

In column 5, line 26, please change "bond marrow," to -- bone, bone marrow, --.

UNITED STATES PATENT AND TRADEMARK OFFICE
CERTIFICATE OF CORRECTION

PATENT NO.  : 5,071,741
DATED       : December 10, 1991
INVENTOR(S) : Brockbank, Kelvin G.M.

It is certified that error appears in the above-identified patent and that said Letters Patent is hereby corrected as shown below:

In column 7, line 66, please change "bl" to -- 1 --.

In column 9, line 67, claim 15, please change "tissue" to -- tissue, --.

In column 10, line 43, claim 23, please change "post-transplantable" to -- post-transplant --.

In column 11, line 1, claim 25, please change "The" to -- A --.

In column 12, line 15, claim 28, please change "a" to -- an --.

Signed and Sealed this

Sixth Day of July, 1993

Attest:

MICHAEL K. KIRK

*Attesting Officer*   *Acting Commissioner of Patents and Trademarks*

UNITED STATES PATENT AND TRADEMARK OFFICE
CERTIFICATE OF CORRECTION

PATENT NO. : 5,071,741
DATED : December 10, 1991
INVENTOR(S) : Kelvin G.M. Brockbank It is certified that error appears in the above-identified patent and that said Letters Patent is hereby corrected as shown below:

Column 10, line 25, change "cell" to --gel--.

Signed and Sealed this

Seventh Day of September, 1993

Attest:

BRUCE LEHMAN

Attesting Officer     Commissioner of Patents and Trademarks